United States Patent
Green et al.

(10) Patent No.: US 6,472,885 B1
(45) Date of Patent: Oct. 29, 2002

(54) METHOD AND APPARATUS FOR MEASURING AND CHARACTERIZING THE FREQUENCY DEPENDENT ELECTRICAL PROPERTIES OF DIELECTRIC MATERIALS

(76) Inventors: Christopher Charles Green, 14625 S. Mountain Pkwy. #2009, Phoenix, AZ (US) 85044; Jeffrey Max Seligman, 3737 N. Country Club Apt. 215N, Tucson, AZ (US) 85716

( * ) Notice: Subject to any disclaimer, the term of this patent is extended or adjusted under 35 U.S.C. 154(b) by 0 days.

(21) Appl. No.: 09/690,322

(22) Filed: Oct. 16, 2000

(51) Int. Cl.$^7$ .............................. G01R 27/32; H01P 5/18
(52) U.S. Cl. ...................... 324/638; 324/646; 333/115
(58) Field of Search ................................. 324/638, 601, 324/603, 639, 642, 76.22, 646; 702/85; 333/115, 116, 246; 343/785; 257/691

(56) References Cited

U.S. PATENT DOCUMENTS 5,625,328 A * 4/1997 Coleman ..................... 333/116
5,773,985 A * 6/1998 Bradley ....................... 324/638

OTHER PUBLICATIONS

W.S. Weir, "Automatic Measurement of Complex Dielectric Constant and Permeability at Microwave Frequencies", Proceedings of the IEEE, vol. 62, No. 1, pp. 33–36, Jan., 1974.

W. Barry, "A Broadband Automated Stripline Technique for the Simultaneous Measurement of Complex Permittivity and Permeability", IEEE Transactions on Microwave Theory and Techniques, vol. MTT–34, No. 1, pp. 80–84, Jan. 1986.

J. Baker–Jarvis, Bill F. Riddle, "Dielectric Measurements Using a Re–entrant Cavity: Mode–Matching Analysis", National Institute of Standards and Technology Note 1384, Boulder, CO, Nov. 1996.

D. Dube, M.T. Lanagan, J.H. Kim, and S.J. Jang, "Dielectric Measurements on Substrate Materials at Microwave Frequencies Using a Cavity Perturbation Technique", Journal of Applied Physics, vol. 63, No. 7, pp. 2466–2468, Apr. 1988.

Hewlett Packard Company "Permittivity Measurements of PC Board and Substrate Materials Using the HP4291A and H16453A", Doc. #5962–6973E, Feb. 1994.

* cited by examiner

*Primary Examiner*—N. Le
*Assistant Examiner*—James C. Kerveros
(74) *Attorney, Agent, or Firm*—Lawrence Edelman (57) ABSTRACT

A method and apparatus for measuring complex permittivity of dielectric materials in solid, liquid, or gas form. The apparatus is includes a TEM or quasi-TEM transmission line test fixture, which contains the dielectric material under test, a set of unique reflective load assemblies for inducing reflections in the fixture, an analyzer that measures magnitude and phase, a custom calibration kit, and a computer with computational software. The method begins by sequentially placing the set of load assemblies at the input of the analyzer. One port s-parameters are then obtained. Next, the set of load assemblies is sequentially placed at one end of the test fixture while the other end of the fixture is placed at the input of the analyzer and one port s-parameters are then obtained. Connectors are coupled to both ends of the fixture. A computer then executes a program to solve a set of equations constructed from the s-parameter data for computing input reflection coefficients. The program also de-embeds and mathematically curve-fits a specified electrical model of the transmission line to best replicate the reflection coefficients. Complex permittivity is calculated from the computed impedance values of the model.

20 Claims, 10 Drawing Sheets

*Hardware Modules*

*Software Modules*

Fig. 3a

Fig. 3b $$S_{11n} = \Gamma_0[1 - \Gamma_{Ln}^2 A_1^4 A_L^4] + \Gamma_1[A_1^2 - \Gamma_{Ln}^2 A_1^2 A_L^4] + \Gamma_{Ln}^2 A_1^2 A_L^4$$

Where,
- $A_1$ is the propagation factor inside the transmission line test fixture
- $A_L$ is the propagation factor inside the coax section of the load assembly
- $\Gamma_1, \Gamma_2, \Gamma_3$ are reflection coefficients at different points as shown and, $$A_1 = e^{-\gamma_1 l_1} \; ; \; A_2 = e^{-\gamma_2 l_2}$$

Where,
- $\gamma_1, \gamma_2$ are propagation constants of the respective lines and,
- $l_1, l_2$ are the line lengths

Where, $R_s$ = series resistance of the model
$R_p$ = parallel resistance of the model
$X_s$ = series reactance of the model
$X_p$ = parallel reactance of the model
f = signal frequency
c = speed of light in a vacuum
$\varepsilon_0$ = 8.854 x $10^{-12}$ Farad/meter $Z_s = R_s + jX_s$ (Ω)

$Z_p = R_p + jX_p$ (Ω)

$\varepsilon = \varepsilon' - j\varepsilon''$ $\varepsilon' = \varepsilon_0 \left[ \dfrac{-2c^2 X_s}{l^2 \pi^2 f^2 X_p} \right]$ $\varepsilon'' = \varepsilon_0 \left[ \dfrac{2c^2 X_s R_p}{l^2 \pi^2 f^2 X_p^2} \right]$

Fig. 5b

Arbitrary filter structure (L-section depicted)

Where, $R_s$ = series resistance of the model
$R_p$ = parallel resistance of the model
$X_s$ = series reactance of the model
$X_p$ = parallel reactance of the model
$\varepsilon_0$ = 8.854 x 10$^{-12}$ Farad/meter $$\varepsilon = \varepsilon' - j\varepsilon''$$

$$Z_s = R_s + jX_s \quad (\Omega)$$

$$Z_p = R_p + jX_p \quad (\Omega)$$

Fig. 5c

METHOD AND APPARATUS FOR MEASURING AND CHARACTERIZING THE FREQUENCY DEPENDENT ELECTRICAL PROPERTIES OF DIELECTRIC MATERIALS

CROSS-REFERENCE TO RELATED APPLICATIONS

Not applicable.

BACKGROUND—Field of Invention

This invention relates to a method and apparatus used for determining the dielectric properties of materials, in particular the complex permittivity ($\epsilon$) and loss tangent (tan $\delta$).

BACKGROUND—Description of Prior Art

The ultimate importance of determining the complex permittivity and loss tangent of materials over frequency is to better predict the behavior of signals propagating along a transmission line, bond wire, or nearly any type of waveguide. Knowledge of propagation speed and attenuation is key to many circuit designs. In high-speed digital applications, knowing the behavior of the complex permittivity over a frequency range is the key to predicting dispersion. Signal integrity can be better understood by examining each Fourier component.

There are several different types of test methods that have been invented over the years for determining the complex permittivity and loss tangent of dielectric materials. Most use complicated fixtures, specialized test equipment and software. All methods employ their own special equations for computational purposes.

One common method for determining the complex permittivity is called the T/R method. Weir (1) and Barry (2) provide method details. In essence, the measurement setup consists of a slab of dielectric material inserted into an air-filled coax transmission line or waveguide. An analyzer is used to perform 2 port measurements on this setup and provides the electrical signals as well as the measurement capability. Based on a set of boundary conditions and the four sets of s-parameters, the transmission and reflection coefficients are solved at the dielectric interface. Based on these parameters, equations are constructed for the complex permittivity and permeability. Information about the sample dimensions and location within the test line must be provided as well.

There are drawbacks to this method. First, the test samples must be machined to precise shapes. For coaxial fixtures, this is rather tedious. Special numerically controlled milling capabilities are required to make the samples just the right cylindrical dimensions. But there will always remain some air gap between the dielectric and the fixture which introduces errors. When using a waveguide fixture, it restricts the measurements to very high frequencies within the narrow band of the waveguide. In both cases, multi-moding must be avoided since the T/R analysis is only valid for the fundamental mode. Another drawback of this method, is that it is a resonance method, so only certain frequencies within a band can be measured depending upon the sample dimensions and fixture size. Determining complex permittivity at different frequencies requires constructing entirely new sets of test fixtures. Another problem is that the analysis breaks down at intervals where the dielectric sample length is a multiple of a half of a wavelength. Plated materials (with metal) cannot be used.

A number of cavity resonance methods have been developed for measuring the dielectric constant. The first method, developed at the National Institute fore Standards and Technology (NIST), uses a coaxial reentry cavity (3). The test setup consists of a coaxial line with a gap in the center conductor. This gap is filled by the dielectric under test. An electric field is created in the gap. Based on field equations and boundary conditions, elaborate mode matching theory is developed and expressions for Q (1/tan $\delta$) and $\epsilon_r$ at resonance frequencies are developed (based on $TM_{0m}$ modes). Losses due to the finite conductivity of the cavity walls are accounted for. An approximate filling factor due to the partially filled cavity is given. This is an additional source of error.

The shortcomings of this method are the fact that Q and $\epsilon_r$ can only be determined at resonant frequencies. In addition, this method is limited to the 100 MHz to 1 GHz band. Special machining of samples is also required. Also, unlike most methods, high loss materials cannot be characterized. This method is good for determining low losses.

The next method discussed is a cavity perturbation technique (4). The test setup consists of a resonant cavity placed on an X-band waveguide. An aperture couples energy into the cavity. This method determines Q for both loaded and unloaded cavities. An explicit expression is provided for the loss tangent and dielectric constant based on the values of Q in the loaded and unloaded case, cavity dimensions, and dielectric dimensions. Q is determined from the half-power bandwidth at each resonant frequency. The measurements are limited to the five different observed resonances of the cavity, all at five different $TE_{1x}$ modes. The frequencies are also limited in the X-band range of 8 to 12 GHz.

One of the most common commercial methods that is available on the market today is the HP4291A RF material impedance analyzer (5). This technique employs an RF parallel plate measurement method to measure impedance. The measurement setup consists of an HP16453A test fixture that sandwiches material between two electrodes to form a dielectric filled capacitor. An independent test system, known as the HP4291A, measures the admittance of this capacitor over frequency, and the internal firmware calculates the complex permittivity $\hat{\epsilon}_r$ based on the following equation:

$$\hat{\epsilon}_r = \frac{Y_m t}{j\omega \epsilon_0 A} = \epsilon'_r + j\epsilon''_r,$$

where $Y_m = G + j\omega C$ is the measured admittance, $\epsilon_0$ is the absolute permittivity of free space, t is the material thickness, and A is the capacitor's plate area. The HP4291A measurement system employs an RF system to measure admittance (voltage÷current). An RF synthesized source is placed in series with the capacitor. A voltmeter placed in parallel with the source measures its complex input signal (V) while a voltmeter placed across a test resistor in series with the capacitor to determine the current (I) through it.

Calibration and fixture compensation routines are required prior to measurements. However, the method may not work for materials that are metallized. The measurement system, software, and test fixtures are very expensive as well. A couple of other fixtures can be purchased with this instrument for the low frequency measurements. This measurement system is limited to 1.5 GHz and subject to air gap errors between the test fixture and the MUT.

SUMMARY

The present invention consists of an apparatus (with software) with the following components:

(a) a TEM or quasi-TEM test fixture;

(b) a set of unique reflective load assemblies, each having a different impedance value;

(c) an s-parameter analyzer (analyzer) that is used to make one port s-parameter measurements of either the test fixture, reflective load assembly, or calibration standards;

(d) a custom calibration kit for establishing the reference plane at the input connector—fixture interface;

(e) one computer used for data acquisition, format data conversion, determining internal reflection coefficients within the system, curve fitting software, and computing complex permittivity;

(f) a second computer which is sometimes internal to the analyzer used for controlling and calibration of the analyzer;

and is used to determine the frequency dependent complex permittivity of dielectric materials by performing the following steps:

(g) assembly of test fixture with MUT;

(h) sequentially placing a set of reflective load assemblies to the analyzer and measuring s-parameters;

(i) sequentially placing the set of reflective load assemblies to the output coaxial connector on the test fixture and measuring s-parameters on the input coaxial connector;

(j) computation of the internal reflection coefficients within the test fixture based on the s-parameter measurements;

(k) de-embedding and mathematical curve-fitting to a specified electrical model of the transmission line;

(l) computation of the complex permittivity of the MUT based on the calculated impedance of elements in the specified electrical model.

OBJECTS AND ADVANTAGES

This patent possesses good attributes. Several objects and advantages of this present invention are:

(a) to provide complex permittivity information over a wide frequency range which is not limited to just a few frequency points;

(b) to eliminate the need for a complex fixture design that is common with so many measurement methods;

(c) to allow users to employ any transmission line test fixture since the method will work with a transmission line of any cross sectional geometry;

(d) to provide the capability of making measurements using test equipment that is already common to many electrical laboratories;

(e) to provide the capability of determining the complex permittivity of not only solids, but liquids and gasses as well;

(f) to allow for the calibration reference plane to be placed at the end of the test fixture when using a microstrip, stripline, or coaxial test fixture for accurate measurement results;

(g) to allow one to place the dielectric under test in actual 'in circuit' test conditions;

(h) to allow one to be able to perform easy temperature testing of the dielectric.

REFERENCE NUMERALS IN DRAWINGS 2 s-parameter Analyzer
5 Computer for functional control of the calibration routines
10 Set of unique complex reflective load assemblies
16 Clamping fastener
20 Upper stripline plate
24 Connector
28 Dowel alignment pin
32 Pin tab
36 Low loss dielectric pressure plate
40 Coax center conductor
44 Connector flange
48 Plug
52 Threaded hole
56 Calibration phase reference plane
60 Model series inductance
64 Model shunt capacitance
68 Model series impedance
72 Arbitrary filter structure
4 Computer with software
6 50 ohm matched terminating load
8 Test fixture
12 Custom calibration kit
14 Connector protection/alignment pin
18 Clamping fastener
22 Strip conductor
26 Lower stripline plate
30 Dielectric under test
34 Connector flange
38 Microstrip plate
42 Coax center connector insert
46 Dielectric under test (solid form)
50 Connector
54 Outer coaxial conductor
58 Coax cable
62 Model series resistance
66 Model shunt conductance
70 Model parallel impedance

Figure 1:
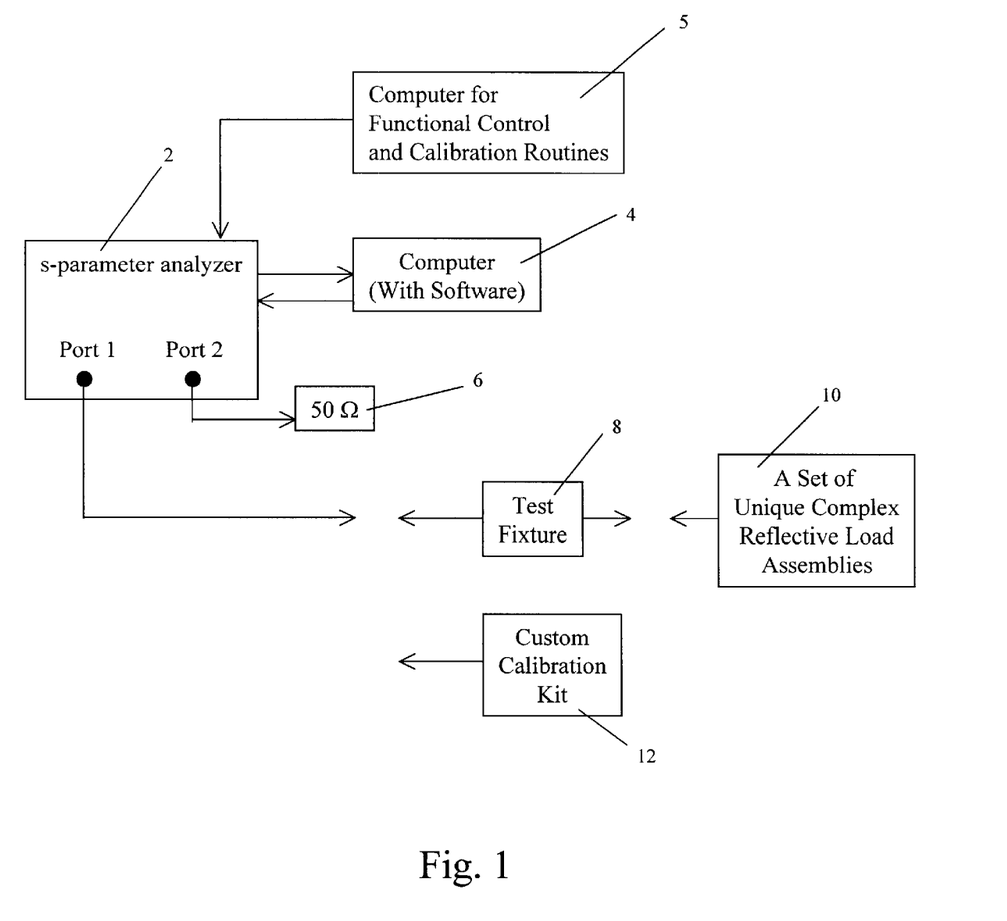
FIG. 1 shows the entire measurement apparatus used for determining the complex permittivity of materials.
Figure 2A:
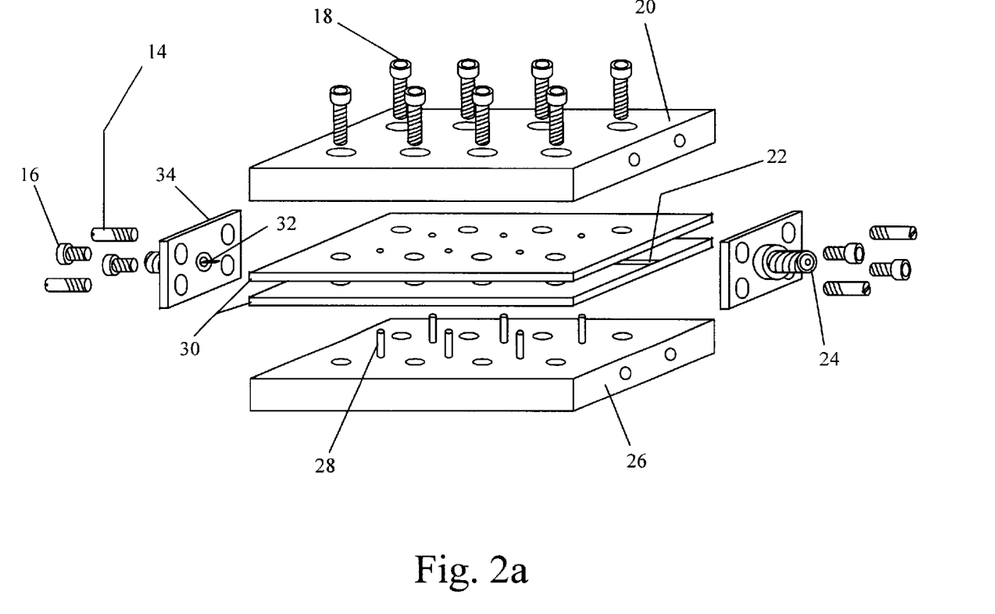
FIG. 2a shows a test fixture in the stripline configuration that contains the dielectric material under test supports transverse electromagnetic waves (TEM waves).
Figure 2B:
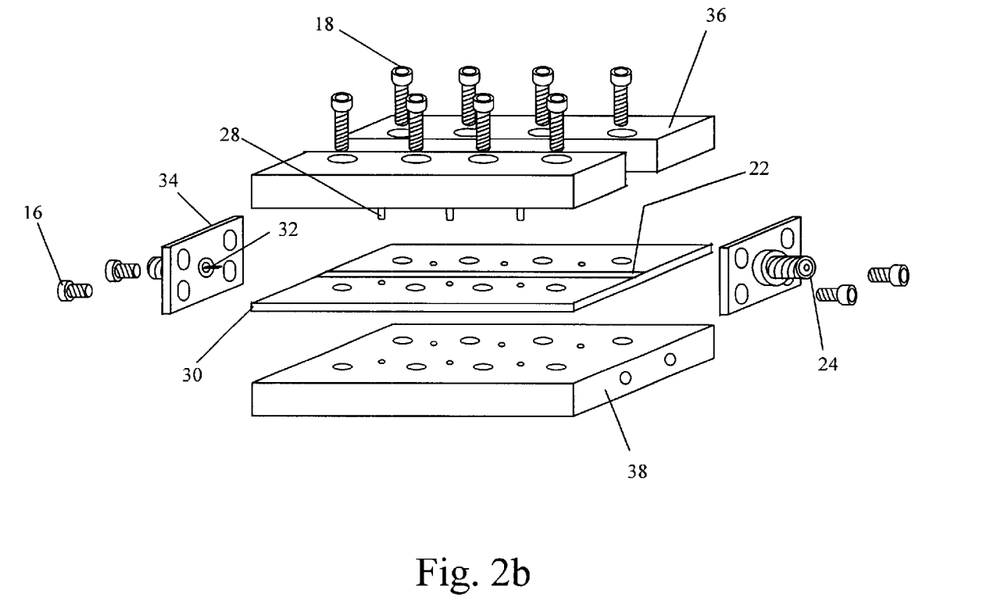
FIG. 2b shows a test fixture in the microstrip configuration that contains the dielectric material under test and supports quasi-TEM waves.
Figure 2C:
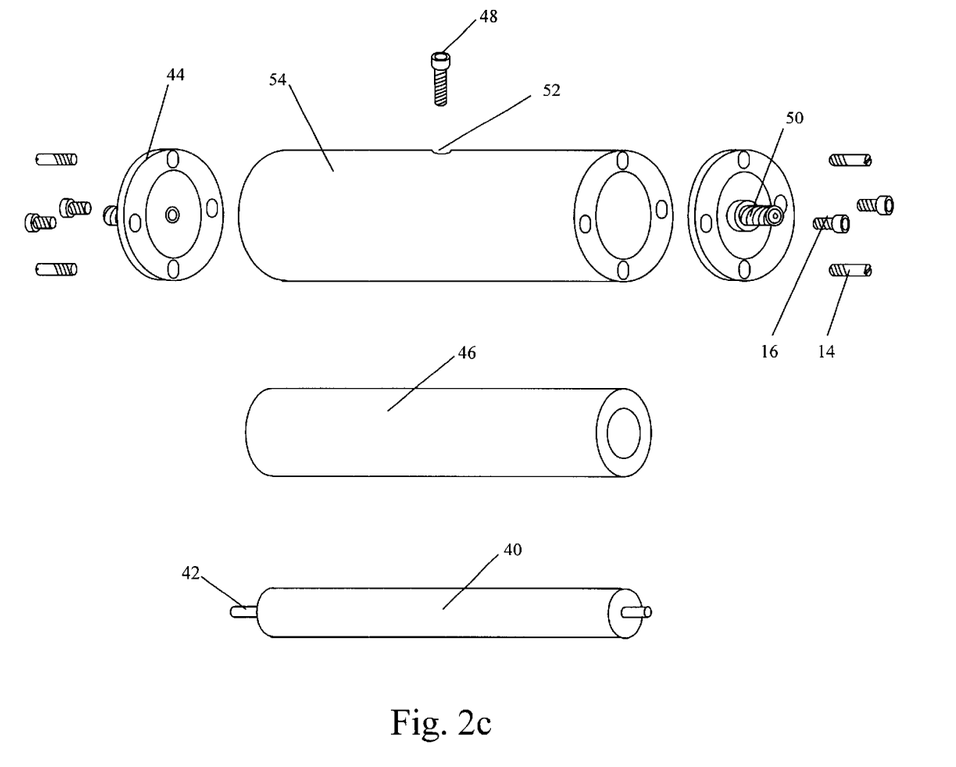
FIG. 2c shows a test fixture in the coaxial configuration that contains the dielectric material under test (MUT) and supports TEM waves.

DESCRIPTION—FIG. 1, 2a, 2c—Preferred Embodiment

The preferred embodiment of the apparatus used for obtaining the complex permittivity is illustrated in FIG. 1.

The apparatus employs a s-parameter analyzer 2 which provides the means of measuring s-parameters within the system and the electrical signals. The analyzer has two ports for such a purpose. Test port cables from the analyzer connect to the desired structure. Since only 1 port measurements are taken, one of the ports is terminated in a 50Ω load 6 and not used. The other port is used to connect to the test fixture 8, to a set of unique complex reflective load assemblies 10, or for connecting to calibration standards from the custom calibration kit 12.

Two computers are used in the apparatus: one for extracting the s-parameter measurements from the analyzer, data conversion of the s-parameter data to a suitable file format, and curve fitting software 4, and another computer for functional control of the analyzer which includes calibration routines 5. The analyzer uses the custom calibration kit 12 to establish accurate phase reference planes at the connector interfaces on the test fixture.

The unique complex reflective load assemblies 10 have different impedance values from each other. They are also suitably different from the transmission line impedance of the test fixture 8. The physical load assemblies consist of a transmission line coax section connected to a load.

FIGS. 2a and 2c show exploded views of the preferred embodiments of the test fixture 8 contained within the apparatus. The test fixture shown in FIG. 2a has upper 20 and lower 26 stripline plates which serve as the outer conductor of the stripline transmission line. The inner conductor is a thin strip conductor 22. Connectors 24 are used to interface the fixture to a test port cable which connect to one of the analyzer ports. There is a small pin tab 32 that protrudes out of the connector that rests on the thin strip conductor. It allows an electrical connection to be made between the inner conductor of the stripline transmission line fixture and the inner conductor of the test port cable. The dielectric material under test 30 rests between the plates to act as the transmission line's insulator. Optional dowel pins 28 can be used for alignment purposes. Clamping fasteners 18 are used to hold the entire fixture together by pulling the two plates together. A different set of clamping fasteners 16 are used to hold the connectors to the ends of the fixture by its flange 34. Connector protection/alignment pins 14 are used to protect the connector's pin tab in the assembly process and serve no other purpose.

The test fixture shown in FIG. 2c has an outer cylindrical tube that serves as the outer conductor 54 of the coaxial transmission line. The coax center conductor 40 of the transmission line is also metal. It has two center connector inserts 42 on its ends which get inserted into the back end of the connector 50 during the assembly process. The dielectric under test 46 in solid form rests between the center conductor 40 and the outer conductor 54. Clamping fasteners 16 and connector protection/alignment pins 14 are also used for the same purposes as the stripline fixture. This fixture allows for liquids and gasses to be tested as well. In this case, no dielectric under test 46 in solid form is assembled in the fixture. Instead, the fixture is assembled with no dielectric. Liquid, or gas is inserted into a hole 52 after assembly and then plugged 48.

FIG. 2b—Alternative Embodiment

FIG. 2b shows an alternative embodiment of the test fixture in microstrip form. The same fixture used for the stripline fixture can be used for the microstrip fixture giving it dual capabilities. In the case of a microstrip, only one dielectric slab 30 is required. Quasi-TEM waves are supported in this structure. TEM waves are supported in the preferred embodiments. All the purposes of the components are identical to that of the stripline. The only additional components added to the microstrip are the low loss dielectric pressure plates 36 used for holding the fixture together for added stability. No top plate is used in the microstrip fixture. The strip conductor is exposed to the outside air.

In FIG. 1, the unique set of loads within the apparatus may be replaced with a load pull system. A load pull system provides any desired load impedance. The plurality of impedance values may be programmed into the load pull controller unit of the load pull system so the entire measurement process can be fully automated.

Operation—FIGS. 1, 3, 4, 5

Figure 3A:
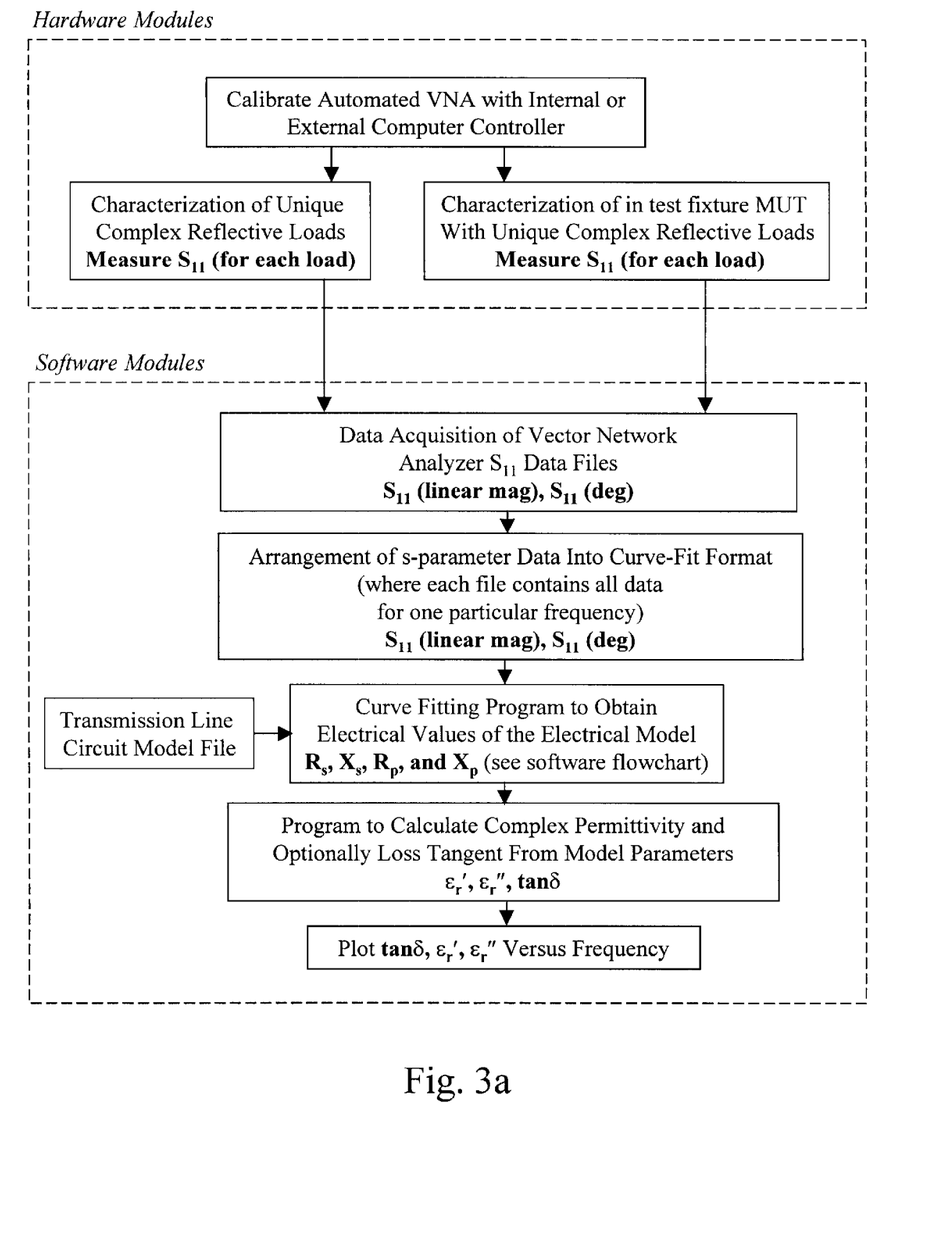
FIG. 3a is a flowchart for using the entire apparatus for determining the complex permittivity of the dielectric MUT.

FIG. 3a shows the operational steps of this apparatus shown in FIG. 1. First, the s-parameter analyzer 2 is calibrated over a specified frequency range with the custom calibration kit 12. An internal or external computer 5 for functional control runs the calibration routines.

Next, the set of loads 10 is measured sequentially for their s-parameter ($S_{11}$) values. These loads are arbitrary and their values have purposely been chosen to be mismatched with respect to the characteristic impedance of both the transmission line test fixture and the analyzer. The test fixture 2, which contains the dielectric material under test, is then terminated sequentially with each of these loads and measured for their $S_{11}$ values. The impedance of the transmission line test fixture is not equal to that of the analyzer cables or any of the test loads. This arrangement induces multiple reflections within the test system, returning an appreciable amount of the signal back to the analyzer at all frequencies over the entire specified frequency range. The impedance of the test fixture was purposely made to be different than the impedance of the measurement system and reflective load assemblies. After each measurement taken, another computer 4 with data acquisition software extracts the raw data.

After all the raw data has been obtained, a program on this same computer is then used to rearrange the two sets of s parameter data that have been previously obtained from the fixture and the loads. It converts the data into a format acceptable for the next level of processing. Separate files are created to hold all data for each individual frequency point.

Figure 5A:
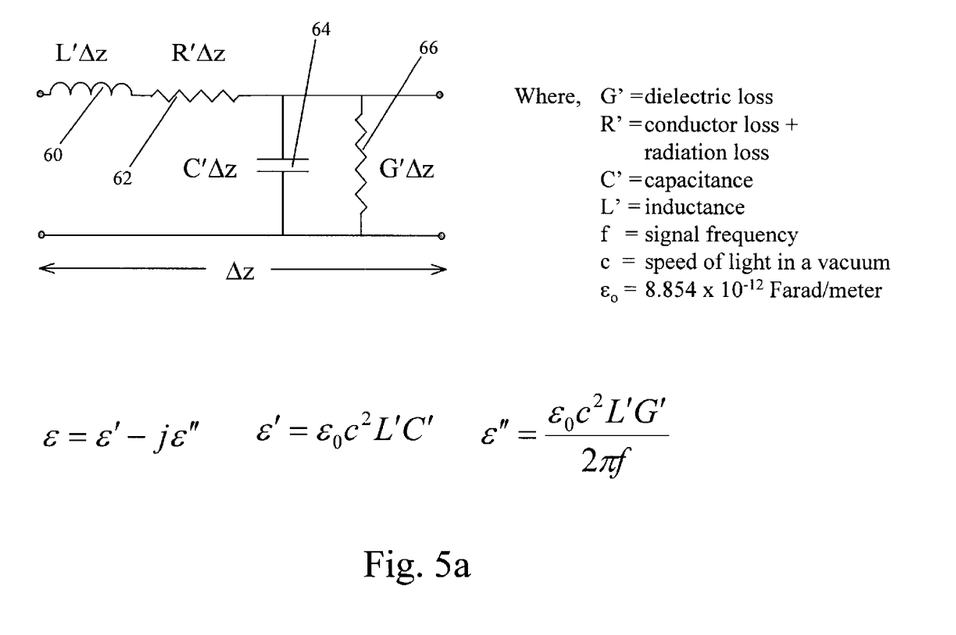
FIG. 5a shows the classic lumped element transmission line circuit model used in the formulation process.
Figure 5B:
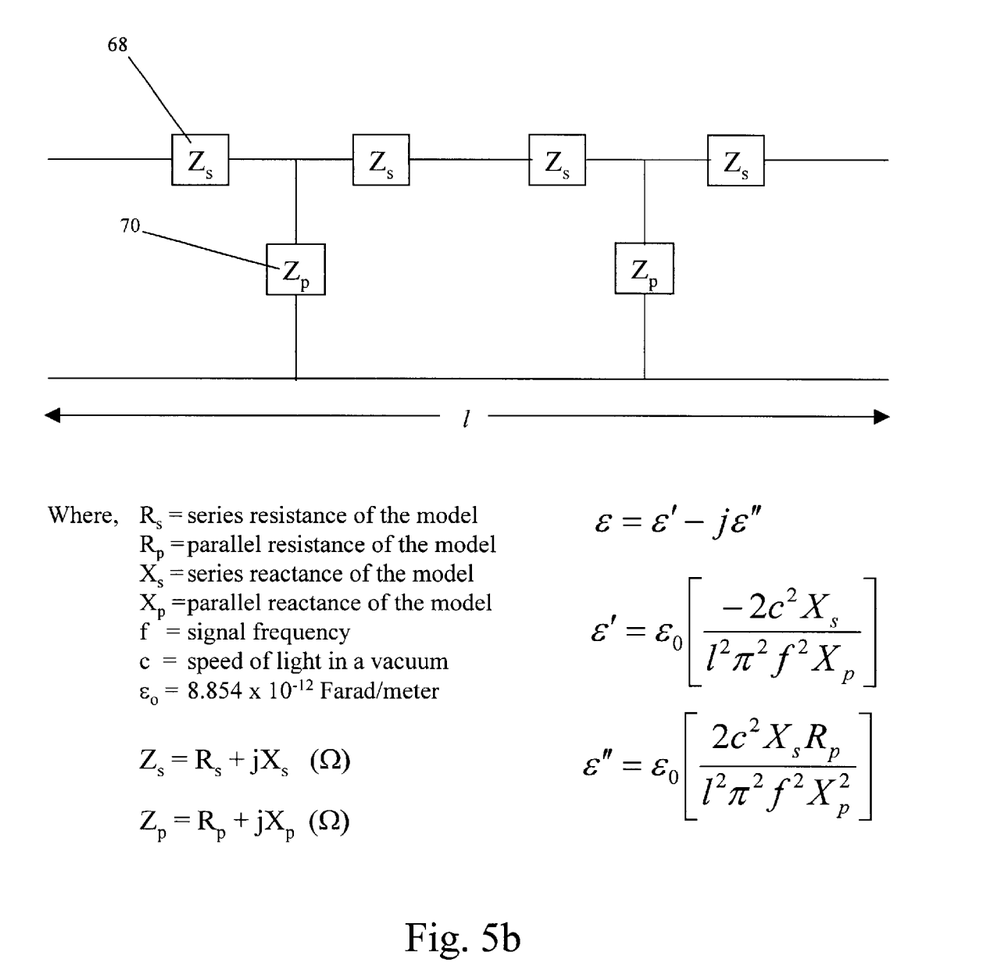
FIG. 5b shows a T-section transmission line circuit model that can be specified by the user.
Figure 5C:
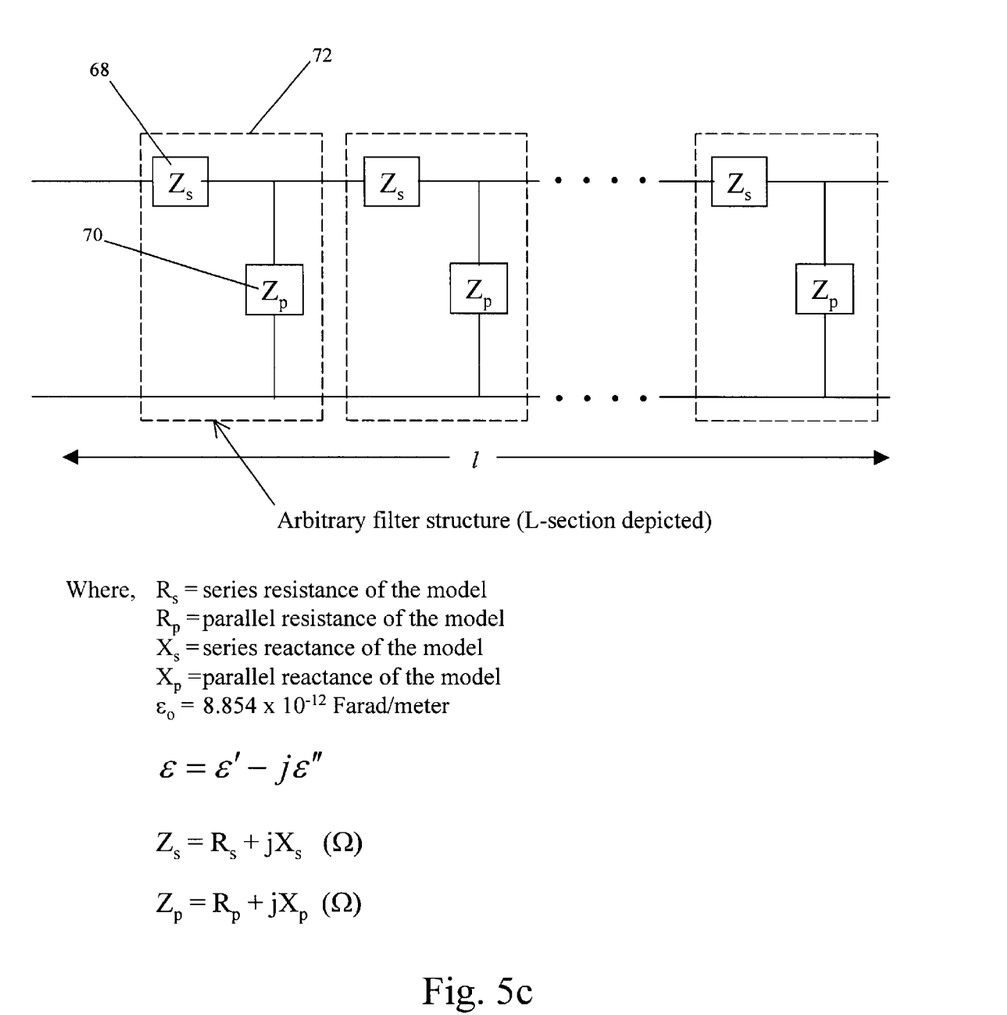
FIG. 5c shows a general transmission line circuit model that can be specified by the user.

The topology of a transmission line circuit model for the test fixture must be provided by the user before the computer optimization program can operate on the data. The program allows for the selection from a number of circuit configurations composed of series $Z_s$, and shunt $Z_p$. For the preferred embodiment of this work, two identical, symmetrical, lossy, low pass T-sections are cascaded. Each T-section is made up of a series impedance $Z_s$ and a shunt impedance $Z_p$ as shown in FIG. 5c. The reason why a transmission line model should be used to model the behavior of a transmission line fixture is because it contains both series impedances $Z_s$, that can represent series resistance $R_s$, and inductance $X_s$, and shunt impedances $Z_p$, that can represent parallel capacitance $X_p$ and finite resistance $R_p$. $R_s$ corresponds to conductor loss, $X_s$ corresponds to the transmission line inductive reactance, $R_p$ corresponds to the loss in the dielectric material, and $X_p$ corresponds to the capacitive reactance shunting the line.

Figure 3B:
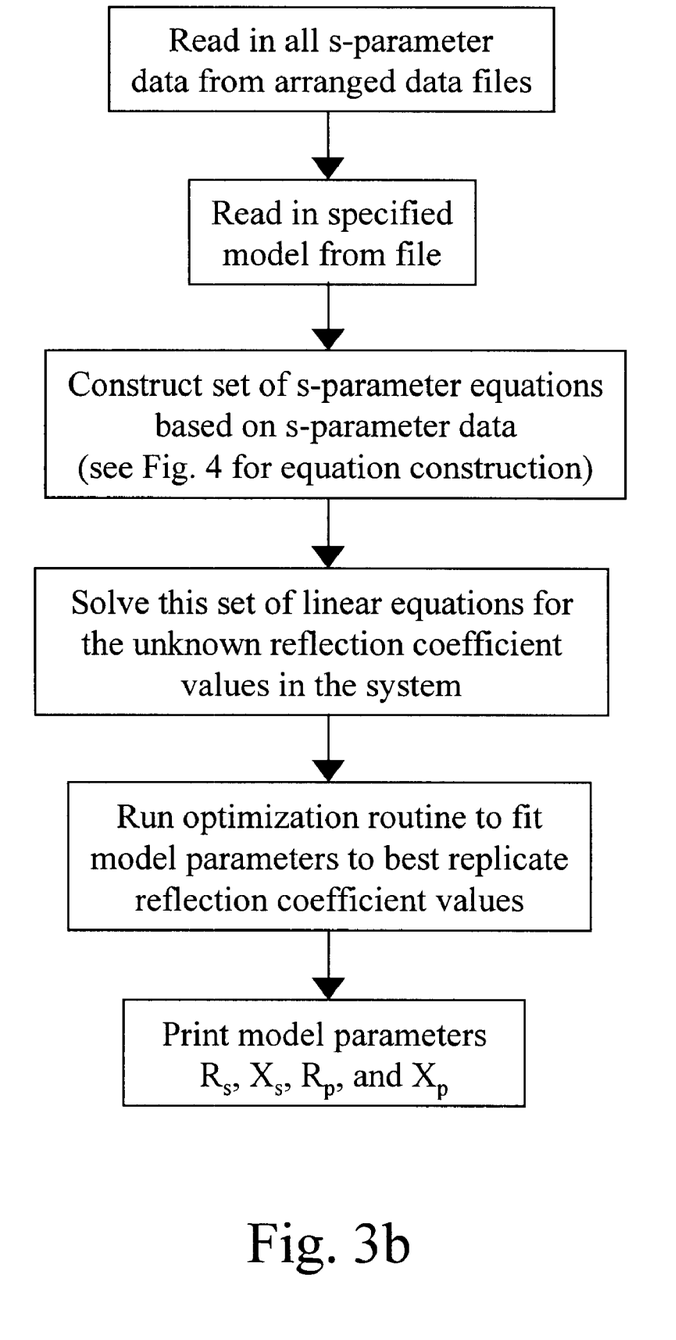
FIG. 3b is a flowchart of the curve-fitting software, which shows the steps for computing the electrical model parameters from the raw s-parameter data.
Figure 4:
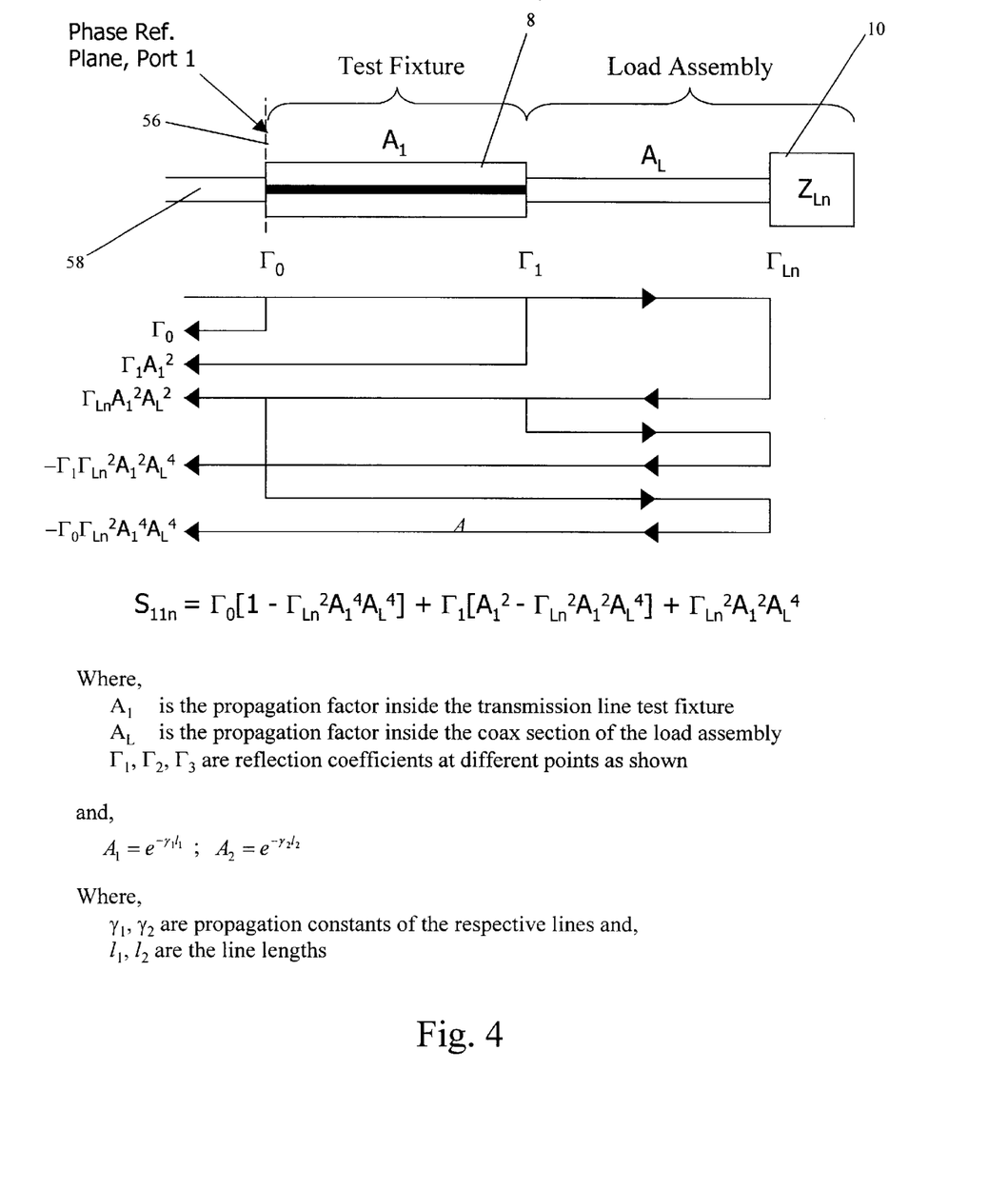
FIG. 4 shows a diagram of all the reflections taken into account and the equation used for computing the internal reflection coefficients.

Once this model has been specified, it is combined with the S-parameter test data and then loaded into a curve-fitting program on the same computer 5. FIG. 3b gives a detail of the operational steps of the program. After reading the prearranged s-parameter data and the specified model file, the program constructs a set of linear equations and solves for the two internal reflection coefficients of the test fixture. FIG. 4 shows the set of reflections that are used to construct the equations, which are shown. Five different reflection patterns are taken into account. Higher order reflections, such as signals that are the result of more than one reflection off the transmission line interfaces are sufficiently enervated.

Once the reflection coefficients have been calculated, the optimization program uses an iteration method to achieve a best fit of the impedance model parameters $Z_s$ and $Z_p$ to this reflection coefficient data. It includes a synthesis/optimization program, which determines the best values for the individual circuit elements.

Once the model parameters have been optimized and recorded, the complex permittivity is calculated according to equations shown in FIG. 5c. In order to calculate the loss tangent, the model parameters ($R_s$, $X_s$, $R_p$, and $X_p$) that were used in the specified model must be fitted to impedance parameters (R', L', G' and C') of the classic lumped element transmission line circuit model shown in FIG. 5a. The equations shown in FIGS. 5b and 5c show these results.

CONCLUSION

The described invention consisted of the following components:

1. Apparatus for making a frequency dependent dielectric material characterization for determining the complex permittivity ($\epsilon=\epsilon'-j\epsilon''$) of the dielectric material comprising:

a TEM or quasi-TEM transmission line test fixture that is comprised of the dielectric material under test (MUT), a center conductor that runs through the MUT, an outer conductor ground plane, an input connector and an output connector coupled to opposite ends of a transmission line formed by the test fixture;

a means for providing sequentially different impedance values to the output coaxial connector, each impedance value being mismatched with respect to that coaxial connector and transmission line, thereby producing definite reflections;

an analyzer coupled in a mismatched manner for measuring s-parameters at said input coaxial connector of said test fixture;

a data acquisition means is coupled to the analyzer for extracting the s-parameter measurements;

a computer responsive to the s-parameter measurements for computing the internal reflection coefficients within said test fixture, de-embedding and mathematically curve-fitting them to a user specified electrical model of the transmission line to best replicate the computed internal reflection coefficients so as to calculate impedance values of elements in the specified electrical model, and computing the complex permittivity of the MUT based on the calculated impedance values of the elements in the specified electrical model;

a second computer for automation wherein the s-parameter analyzer, used for controlling and calibration of the analyzer and measurement system.

2. A method for making a frequency dependent dielectric material characterization for determining the complex permittivity ($\epsilon=\epsilon'-j\epsilon''$) of the dielectric material comprising the following steps:

placing a dielectric material under test (MUT) in a TEM or quasi-TEM transmission line test fixture, having a center conductor that runs therethrough, an outer conductor ground plane, two coaxial connectors, one being called an input connector and the other being called an output connector, that interface to opposite ends of a transmission line formed by the test fixture, and a clamping mechanism;

sequentially placing a set of different impedance values to the analyzer;

measuring s-parameters of said impedance values;

sequentially placing the above set of different impedance values to the output coaxial connector, each impedance value being mismatched with respect to that coaxial connector and transmission line, thereby producing definite reflections;

measuring s-parameters at said input coaxial connector of said test fixture;

computing internal reflection coefficients within said test fixture based on the s-parameter measurements, de-embedding and mathematically curve-fitting to a specified electrical model of the transmission line to best replicate the computed internal reflection coefficients so as to calculate impedance values of elements in the specified electrical model, and computing the complex permittivity of the MUT based on the calculated impedance values of the elements in the specified electrical model;

3. A transmission line test fixture, capable of being configured as a stripline or microstrip transmission line, comprising:

a dielectric material under test (MUT) in sheet-form, sandwiched between upper and lower conductive fixture plates for the stripline configuration, and for the microstrip configuration, the upper plate is replaced by two insulating pressure plates which hold the MUT in place, fasteners to hold the connectors flush against both ends of the fixture plate(s), and a center conductor that runs therethrough.

We claim:

1. A method for making a frequency dependent dielectric material characterization for the purpose of determining the complex permittivity ($\epsilon=\epsilon'-j\epsilon''$) of a dielectric material under test (MUT), comprising the following steps:

placing the MUT in a test fixture that guides electromagnetic energy from an input connector at one end of the test fixture to an output connector at an opposite end of the test fixture, wherein the cross-sectional dimensions of the test fixture can be unknown;

sequentially placing successive ones of a set comprising 3 or more pre-characterized loads of different impedance values, at the output connector, each impedance value being mismatched with respect to the fixture so as to produce definite reflections at the input and output connectors;

measuring the input reflection coefficient, $S_{11}$ at the input connector of said test fixture over a predetermined frequency range for each one of the pre-characterized loads placed at said output connector, and storing said measured reflection coefficient data;

computing first order and second order (i.e., a reflection of a reflection) complex reflection coefficients over said frequency range at connector and/or load interfaces associated with the test fixture, using said measured s-parameter data;

processing said first order and second order complex reflection coefficients to calculate complex impedance values of elements of a specified electrical model of the test fixture over said frequency range; and computing the complex permittivity of the MUT over said frequency range based on the calculated complex impedance values of the elements from the specified electrical model.

2. The method of claim 1, wherein said processing step comprises, de-embedding and mathematically curve-fitting said stored reflection coefficient data to a specified electrical model of the test fixture which best replicates the computed internal reflection coefficients, so as to calculate complex impedance values of elements of the specified electrical model over said frequency range.

3. The method of claim 1, wherein said complex permittivity comprises a real part and an imaginary part, and the loss tangent, tan δ is computed by taking the ratio of the imaginary part of the permittivity over the real part of the permittivity.

4. The method of claim 1, wherein when a general transmission line circuit model is used by said processing step, the real part of the permittivity is $$\varepsilon' = \varepsilon_0 \left[ \frac{-N_1 c^2 X_s}{4 l^2 \pi^2 f^2 X_p} \right]$$

and the imaginary part of the permittivity is $$\varepsilon'' = \varepsilon_0 \left[ \frac{N_2 c^2 X_s R_p}{4 l^2 \pi^2 f^2 X_p^2} \right]$$

where, $\varepsilon_0$ is the permittivity in a vacuum equal to $8.854 \times 10^{-12}$ farad/meter, c is the speed of light in a vacuum equal to $2.998 \times 10^8$ meter/second, $X_s$ is the series reactance (Ω) of the specified circuit model, $X_p$ is the parallel reactance (Ω) of the specified circuit model, $R_p$ is the parallel resistance (Ω) of the specified circuit model, l is the length (in meters) of the transmission line test fixture, not including the length of the coaxial connectors, π is 3.142, f is the frequency (1/second) of the injected electrical energy, $N_1$ and $N_2$ depend on the number of elements in the specified circuit model and for a 2 section T model, $N_1 = N_2 = 8$, and any transmission line circuit model can be used and solved for their equation element values.

5. The method of claim 4, wherein the loss tangent, tan δ is computed by taking the ratio of the imaginary part of the permittivity over the real part of the permittivity, i.e. tan δ=ε"/ε'.

6. The method of claim 1, wherein the MUT is in a liquid or gas form.

7. The method of claim 1, including the step of using a connector calibration kit for establishing a calibration plane at a connector interface of the test fixture.

8. The method of claim 1, wherein said sequentially placing comprises an automated programmable load for providing said set of pre-characterized loads.

9. A method for making a frequency dependent dielectric material characterization for the purpose of determining the complex permittivity (ε=ε'−jε") of a dielectric material under test (MUT), comprising the following steps:

placing the MUT in a test fixture that guides electromagnetic energy from an input connector at one end of the test fixture to an output connector at an opposite end of the test fixture, wherein the cross-sectional dimensions of the test fixture can be unknown;

sequentially placing successive ones of a set comprising 3 or more pre-characterized loads of different impedance values, at the output connector, each impedance value being mismatched with respect to the fixture so as to produce definite reflections at the input and output connectors;

measuring the input reflection coefficient, $S_{11}$ at the input connector of said test fixture over a predetermined frequency range for each one of the pre-characterized loads placed at said output connector, and storing said measured reflection coefficient data;

computing multiple internal reflection coefficients within said test fixture for each of the different pre-characterized loads sequentially placed at the output connector, processing the computed reflection coefficients so as to fit them to a user specified electrical model of the transmission line which best replicates the computed internal reflection coefficients, so as to calculate impedance values of elements in the specified electrical model, and computing the complex permittivity of the MUT based on the calculated impedance values of the elements in the specified electrical model.

10. The method of claim 9, wherein said processing step comprises, de-embedding and mathematically curve-fitting said stored reflection coefficient data to a specified electrical model of the test fixture which best replicates the computed internal reflection coefficients, so as to calculate complex impedance values of elements of the specified electrical model over said frequency range.

11. The method of claim 9, wherein said complex permittivity comprises a real part and an imaginary part, and the loss tangent tan δ is computed by taking the ratio of the imaginary part of the permittivity over the real part of the permittivity.

12. The method of claim 9, wherein when a general transmission line circuit model is used by said processing step, the real part of the permittivity is $$\varepsilon' = \varepsilon_0 \left[ \frac{-N_1 c^2 X_s}{4 l^2 \pi^2 f^2 X_p} \right]$$

and the imaginary part of the permittivity is $$\varepsilon'' = \varepsilon_0 \left[ \frac{N_2 c^2 X_s R_p}{4 l^2 \pi^2 f^2 X_p^2} \right]$$

where, $\varepsilon_0$ is the permittivity in a vacuum equal to $8.854 \times 10^{-12}$ farad/meter, c is the speed of light in a vacuum equal to $2.998 \times 10^8$ meter/second, $X_s$ is the series reactance (Ω) of the specified circuit model, $X_p$ is the parallel reactance (Ω) of the specified circuit model, $R_p$ is the parallel resistance (Ω) of the specified circuit model, l is the length (in meters) of the transmission line test fixture, not including the length of the coaxial connectors, π is 3.142, f is the frequency (1/second) of the injected electrical energy, $N_1$ and $N_2$ depend on the number of elements in the specified circuit model and for a 2 section T model, $N_1 = N_2 = 8$, and any transmission line circuit model can be used and solved for their equation element values.

13. The method of claim 12, wherein the loss tangent, tan δ is computed by taking the ratio of the imaginary part of the permittivity over the real part of the permittivity, i.e. tan δ=ε"/ε'.

14. The method of claim 9, wherein the MUT is in a liquid or gas form.

15. The method of claim 9, including the step of using a connector calibration kit for establishing a calibration plane at a connector interface of the test fixture.

16. The method of claim 9, wherein said sequentially placing comprises an automated programmable load for providing said set of pre-characterized loads.

17. Apparatus for making a frequency dependent dielectric material characterization for the purpose of determining the complex permittivity ($\epsilon=\epsilon'j\epsilon''$) of a dielectric material under test (MUT), comprising:

a test fixture that guides electromagnetic energy from an input connector at one end of the test fixture to an output connector at an opposite end of the test fixture via said MUT, wherein the cross-sectional dimensions of the test fixture can be unknown;

set of pre-characterized loads of different impedance values for being sequentially placed at the output connector, each impedance value being mismatched with respect to the fixture so as to thereby produce definite reflections at the input and output connectors;

an analyzer for measuring the input reflection coefficient, $S_{11}$, at said input connector of said test fixture over a predetermined frequency range for each one of the pre-characterized loads placed at said output connector, and storing said measured $S_{11}$ data;

a first processing apparatus responsive to said measured $S_{11}$ data for computing over said frequency range first order and second order complex reflection coefficients at connector and/or load interfaces associated with the test fixture, and using said first order and second order complex reflection coefficients to calculate complex impedance values of elements of a specified electrical model of the test fixture over said frequency range; and a second processing apparatus responsive to the complex impedance values of elements calculated by the first processing apparatus, for computing the complex permittivity of the MUT over said frequency range.

18. The apparatus of claim 17, wherein said second processing apparatus de-embeds and mathematically curve-fits the reflection data to a user specified electrical model of the transmission line which best replicates the computed reflection coefficients at the connector and/or load interfaces associated with the test fixture, so as to calculate the complex impedance values of elements of the specified electrical model over said frequency range.

19. The apparatus of claim 17, wherein said first and second processing apparatus comprises a single computer.

20. The apparatus of claim 17, including a controller for automatically controlling said placing of the pre-characterized loads at said output connector.

\* \* \* \* \*